(12) United States Patent
Yu et al.

(10) Patent No.: US 11,813,118 B2
(45) Date of Patent: Nov. 14, 2023

(54) LOUPE-BASED INTRAOPERATIVE FLUORESCENCE IMAGING DEVICE FOR THE GUIDANCE OF TUMOR RESECTION

(71) Applicant: University of Kentucky Research Foundation, Lexington, KY (US)

(72) Inventors: Guoqiang Yu, Lexington, KY (US); Thomas A. Pittman, Lexington, KY (US); Chong Huang, Lexington, KY (US); Nick McGregor, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 582 days.

(21) Appl. No.: 16/629,340

(22) PCT Filed: Jul. 10, 2018

(86) PCT No.: PCT/US2018/041418
§ 371 (c)(1),
(2) Date: Jan. 8, 2020

(87) PCT Pub. No.: WO2019/014205
PCT Pub. Date: Jan. 17, 2019

(65) Prior Publication Data
US 2021/0038339 A1    Feb. 11, 2021

Related U.S. Application Data

(60) Provisional application No. 62/530,613, filed on Jul. 10, 2017.

(51) Int. Cl.
*A61B 90/30* (2016.01)
*G02B 7/00* (2021.01)
(Continued)

(52) U.S. Cl.
CPC .............. *A61B 90/30* (2016.02); *G02B 5/205* (2013.01); *G02B 7/006* (2013.01); *G02B 25/004* (2013.01);
(Continued)

(58) Field of Classification Search
CPC ......... A61B 90/30; A61B 90/20; A61B 90/50; A61B 5/0071; A61B 5/0086;
(Continued)

(56) References Cited

U.S. PATENT DOCUMENTS

| 5,042,930 A | 8/1991 | Hutt |
| 8,786,689 B1 | 7/2014 | Liu |

(Continued)

OTHER PUBLICATIONS

Chen et al "The Head-Mounted Microscope: A Potential Precision Improvement in Phonomicrosurgery"; Laryngoscope 122: Apr. 2012, p. 781-784. (Year: 2012).*

(Continued)

*Primary Examiner* — Jie Lei
(74) *Attorney, Agent, or Firm* — Stites & Harbison PLLC; Warren D. Schickli (57) ABSTRACT

This application concerns a loupe-based wearable device that is enhanced by a mounted visualization aid on the housing body of at least one of the loupe eyepieces, the aid providing a dual light source, a beam splitter, and a camera directed in the same optical path as a user's eyesight such that both visible light and fluorescent dye exciting light can be directed at a site of operation to enhance real time visualization of tissue resection.

18 Claims, 5 Drawing Sheets

(51) Int. Cl.
  *G02B 5/20* (2006.01)
  *G02B 25/02* (2006.01)
  *G02B 25/00* (2006.01)
  *G02C 7/08* (2006.01)
  *A61B 90/20* (2016.01)
  *A61B 90/00* (2016.01)
  *A61B 90/50* (2016.01)

(52) U.S. Cl.
  CPC .............. *G02B 25/02* (2013.01); *G02C 7/086* (2013.01); *A61B 90/20* (2016.02); *A61B 2090/306* (2016.02); *A61B 2090/3616* (2016.02); *A61B 2090/3933* (2016.02); *A61B 2090/3941* (2016.02); *A61B 2090/502* (2016.02)

(58) Field of Classification Search
  CPC ................ A61B 5/0077; A61B 1/0005; A61B 1/000094; A61B 2090/306; A61B 2090/3616; A61B 2090/3933; A61B 2090/3941; A61B 2090/502; G02B 7/00; G02B 5/00; G02B 25/00; G02B 5/205; G02B 7/006; G02B 25/004; G02B 7/002; G02B 21/0012; G02B 21/02; G02B 21/06; G02B 21/365; G02B 21/361; G02B 21/367; G02B 25/02; G02C 7/08; G02C 7/086; G02C 2200/02
  USPC ....... 359/481, 368, 375, 385, 358, 802, 826; 351/41, 155, 159.01, 205, 206, 210, 221; 600/249, 473, 476
  See application file for complete search history.

(56) References Cited

U.S. PATENT DOCUMENTS

| | | | |
|---|---|---|---|
| 8,810,907 B2* | 8/2014 | Haisch | G02B 21/365 359/388 |
| 8,998,609 B2 | 4/2015 | Prakash et al. | |
| 2004/0070823 A1 | 4/2004 | Radna | |
| 2005/0152029 A1* | 7/2005 | Endo | G02B 21/16 359/383 |
| 2005/0182327 A1 | 8/2005 | Petty et al. | |
| 2010/0210951 A1 | 8/2010 | Rahman et al. | |
| 2010/0305436 A1 | 12/2010 | Chen et al. | |
| 2010/0321772 A1* | 12/2010 | Reimer | A61B 90/20 359/385 |
| 2016/0191887 A1 | 6/2016 | Casas | |
| 2017/0099479 A1 | 4/2017 | Browd et al. | |
| 2018/0024341 A1* | 1/2018 | Romanowski | G02B 21/16 359/385 |

OTHER PUBLICATIONS

International Search Report and Written Opinion for PCT/US2018/041418 dated Sep. 25, 2018.

* cited by examiner

LOUPE-BASED INTRAOPERATIVE FLUORESCENCE IMAGING DEVICE FOR THE GUIDANCE OF TUMOR RESECTION

RELATED APPLICATIONS

This application is the national stage of international patent application no. PCT/US2018/041418 filed on Jul. 10, 2018, which in turn claims priority to U.S. Provisional Patent Application 62/530,613, filed Jul. 10, 2017, the contents of all of which are hereby incorporated by reference in their entirety.

FIELD OF THE INVENTION

The present invention concerns new Loupe-based Wearable Fluorescence imaging devices to assist in visualizing target tissue in surgical procedures, such as cancer resection.

BACKGROUND

The most common type of primary malignant brain tumors are malignant gliomas (MGs), accounting for ~40% of all intracranial tumors (National-Brain-Tumor-Society. Tumor types: understanding brain tumors. braintumor.org/brain-tumor-information/understanding-brain-tumors/tumor-types/. 2016). There is compelling evidence that the extent of resection in MGs, including glioblastoma multiforme (GBM), correlates with survival (Kuhnt et al. *Neuro Oncol.* 2011; 13:1339-48; Lacroix et al. *J Neurosurg.* 2001; 95:190-8; McGirt et al. *J Neurosurg.* 2009; 110:156-62; Stummer et al. *J Neurooncol.* 2012; 108:89-97; Stummer et al. *Lancet Oncol.* 2006; 7:392-401; Aldave et al. *Neurosurgery.* 2013; 72:915-20; discussion 920-1; Picart et al. *Neurochirurgie.* 2017; 63:189-196). Consequently, a great deal of effort has been directed toward developing techniques that allow more extensive resections with the goal of improving survival (Rosenthal et al. *Ann Surg.* 2015; 261: 46-55; Acerbi et al. *Neurosurg Rev.* 2014; 37:547-57; Belykh et al. *Front Surg.* 2016; 3:55). Fluorescein, an FDA approved dye, has been extensively used to enhance the identification of MG margins for resection (Acerbi et al. *Acta Neurochir (Wien).* 2013; 155:1277-86; Decker et al. Paper presented at: 19th Annual Scientific Meeting of the Society for Neuro-Oncology; 2014 Miami, Fla.; Long et al. *Expert Rev Mol Diagn.* 2012; 12:383-94). The technique is simple and safe: fluorescein is intravenously injected at the start of the operation, and then an optical imaging device is used to enhance the visibility of fluorescing tumor tissues. Fluorescein-imaging-guided surgeries show significant improvements in gross-total-resection (GTR) rates over conventional surgeries. Based on contrast-enhanced MRI measurements, surgeries using fluorescein imaging achieve GTR rates of 75-100%, which are significantly higher than conventional surgeries with GTR rates of 30-55%. However, most clinical-grade fluorescence imaging systems (e.g., Pentero 900 with YELLOW 560™, Carl Zeiss) are hampered by high costs, limited portability, and lack of flexibility during operation. Moreover, many neurosurgeons prefer and continue to do the resection using wearable magnifying surgical eye loupes, which allow for convenient and fast operation, but are not capable of fluorescence visualization.

There are, however, currently no wearable fluorescence eye-loupes for brain tumor imaging, although a wearable fluorescence goggle has been reported for intraoperative imaging of hepatocellular carcinoma (Mela et al. *Methods Mol Biol.* 2016; 1444:85-95; Mondal et al. *Scientific reports.* 2015; 5:12117; Liu et al. *Transl Res.* 2013; 162:324-31). An initial prototype fluorescence goggle of the present invention was specifically designed for imaging a near-infrared (NIR) fluorescent dye, indocyanine green (ICG) (see FIG. 1). Since NIR light is invisible to human eyes, the surgeon must visualize ICG images using NIR cameras mounted on the goggle. Although effective for some tumors, the goggle-based ICG prototypes still have some major limitations for imaging brain tumors that are addressed by the present invention: (1) unlike surgical eye loupes, the goggle does not provide for adjustable magnification, necessary for neurosurgery; (2) the visualization by NIR cameras mounted on the goggle is different from the more natural ocular view offered by the more commonly used and accepted surgical eye loupes; and (3) ICG lacks specificity in differentiating glial tumors from normal tissue, and the observable time window of ICG is limited to only several minutes (Belykh et al. *Front Surg.* 2016; 3:55), which is likely insufficient for a long, complex neurosurgical procedure. The wearable fluorescence eye-loupe device of the present invention will overcome these obstacles to transform the scientific/surgical field for brain cancer.

SUMMARY OF THE INVENTION

The present invention concerns a loupe-based surgical device for fluorescent and visible light visualization of tissue resection. The device comprises at least one loupe housing body with a magnifying lens placed therein to allow a user to view a target tissue area of a subject; and a mounted visualization aid on the housing body, the aid comprising a dual light source, a beam splitter, and a camera, wherein the dual light source and the camera are focused toward the beam splitter and further wherein the dual light source and camera are oriented to substantially the same field of view of the target tissue after passing through the beam splitter.

The device may further comprise a zoom lens and an optional filter between the camera and the beam splitter. Within the device, the camera may be connected to a computer.

The device may further comprise hinged filters at the viewing end of the loupe housing body. The hinged filters may also comprise ND filter films.

The dual light source may emit individually or simultaneously visible light and a wavelength of light to excite a fluorescent dye. The visible light may be generated by LEDs or by fiber-coupled light with filters. The dual light source may be connected to a control unit that is optionally connected to a foot pedal.

The wavelength of light is selected to excite a fluorescent protein to emit light such as visible light (400-700 nm). The fluorescent protein may be selected from a group consisting of indocyanine green (ICG), blue fluorescent protein (BFP), Tetramethylrhodamine Isothiocyanate (TRITC), cyan fluorescent protein (CFP), wild-type green fluorescent protein (WTGFP), green fluorescent protein (GFP), fluorescein isothiocyanate, yellow fluorescent protein (YEP), Texas Red (TXRED) and cycanine (CY3.5).

The device may further include a lens between the dual light source and the beam splitter.

The present invention also provides a method for visualizing tissue resection, the steps including administering a fluorescent dye to a subject receiving tissue resection; placing the device as described herein on a surgical user operating on the subject; and operating the camera and the dual light source to allow the surgical user to visualize tissue resection in the subject.

DETAILED DESCRIPTION

For malignant brain tumors, the extent of tumor removal (surgical resection) is related to survival. A major limiting factor for complete resection is the ability to identify the complex tumor margins. Multiple imaging solutions (e.g., MRI and CT) have been explored for tumor identification, but these are large and costly modalities and can significantly interfere with the surgical workflow. A new technique, real-time fluorescence imaging, has shown significant improvements in tumor resection rates. The technique is safe and simple: after intravenous injection of an approved fluorescence dye (e.g., fluorescein), an operative microscope equipped with dedicated filters is used to enhance the visibility of tumor margin. However, wide acceptance of this operative microscope is limited by its high cost (~$80K) and poor mobility. Many neurosurgeons prefer to do the resection using only wearable surgical magnifying eye loupes. The invention herein provides a novel, low-cost, wearable, loupe-based, fluorescence imaging technique for easy and accurate identification of tumor margins during surgery, with the goal of reducing positive margin rates and subsequent re-excision surgeries. In this device, compact LEDs and a small CMOS camera with dedicated filters are optically integrated into functional modules for florescence excitation and detection. These lightweight, compact, and inexpensive modules are attached to the surgical loupes to form an all-in-one wearable device allowing for real-time ocular observation and video recording of fluorescence and color images. This low-cost (~$4K), wearable, loupe-based, fluorescence imaging device can achieve the same accuracy as the large expensive operative microscope.

A preliminary prototype (FIG. 3b) that piggybacks on standard surgical eye loupes and a headlight support bracket (see, e.g., FIG. 3a) was initially developed. The prototype comprised a light source, in this case a high-intensity LED, mounted to a support bracket on a loupe device with an illumination source (see FIG. 3b). Filters were placed in front of at least one of the loupes to allow for fluorescence detection. This design provided for easy switching between fluorescence (generated by the mounted light source) and white-light (generated by the Xenon arc lamp coupled into a fiber bundle). In addition, a CCD camera also equipped with another long-pass filter can be attached to the bracket to record fluorescence images for data analysis (i.e., identifying tumor tissues).

A modified device (FIG. 1) provides a miniaturized and lightweight loupe-based device that integrates activating light sources, visible light sources, and the surgeons own field of vision, all able to focus on the same region of interest on a subject. The system can also incorporate a camera to capture and relay the operation to a screen.

A traditional loupe device can be considered to have typically two housing bodies 120 that hold a magnifying lens 121 to a surgeon's eye, often also going through a transparent material, such as a safety lens or prescription eyeglass lens. Such features may be useful to maintain a consistent focal point. The loupe device of the present invention has introduced a mounted device on at least one housing body 121 that provides several features that allow for fluorescence imaging during surgery.

Figure 1:
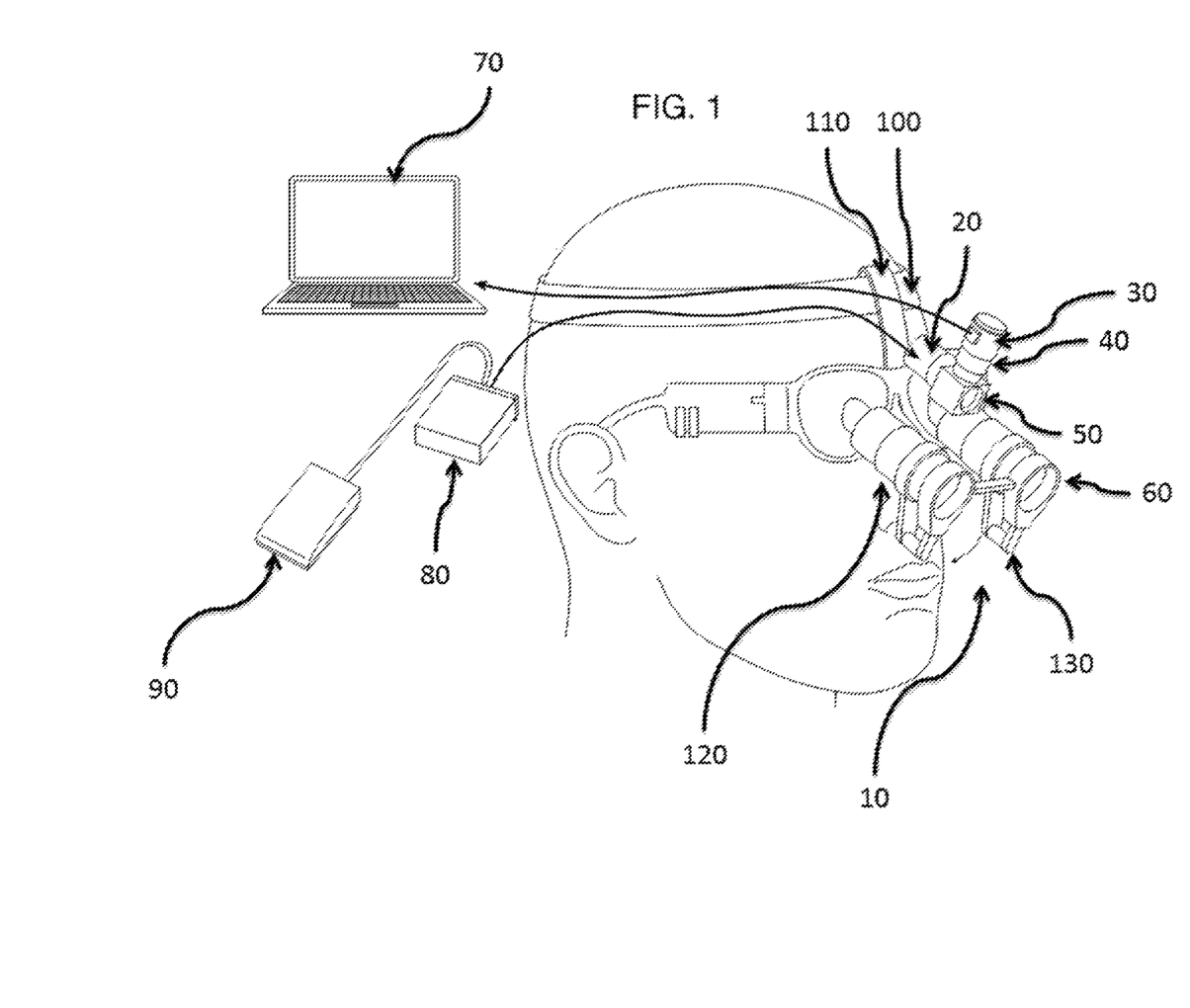
FIG. 1 shows a mechanical design for a wearable, loupe-based, all-in-one modular fluorescence imaging device.
Figure 2:
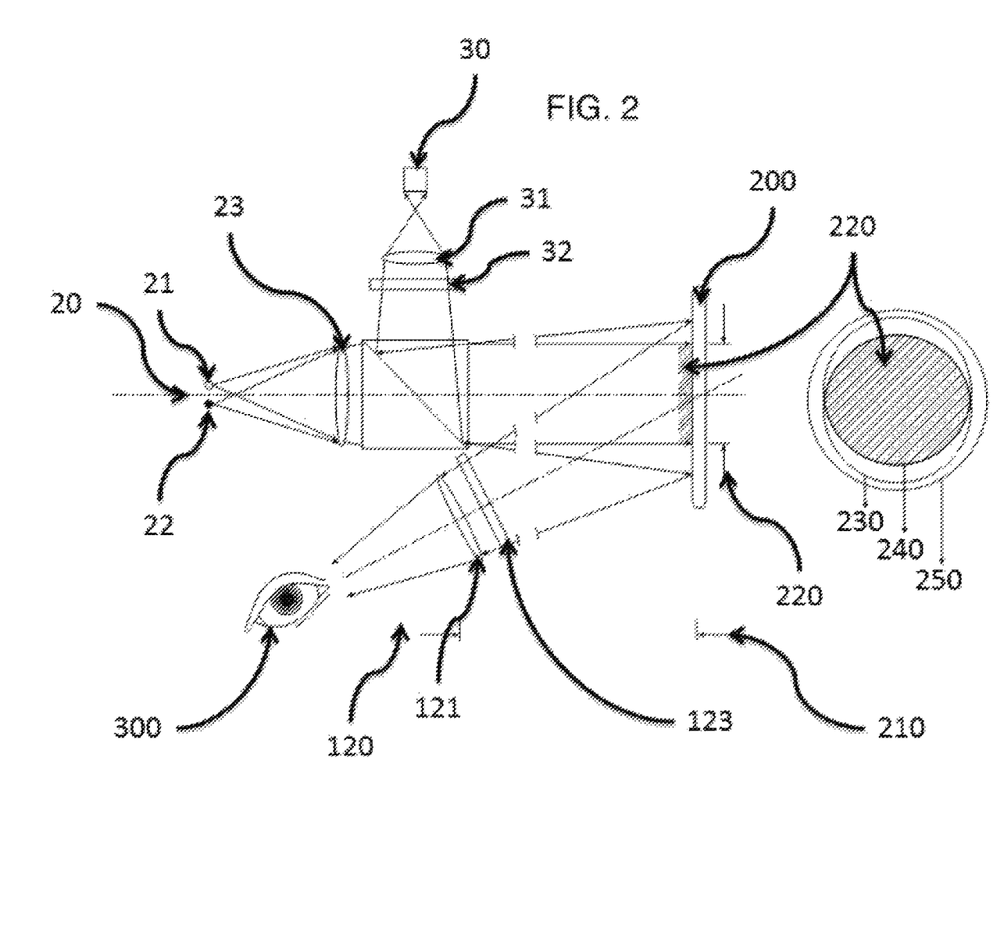
FIG. 2 shows an optical design for a wearable, loupe-based, all-in-one modular fluorescence imaging device.
Figure 3:
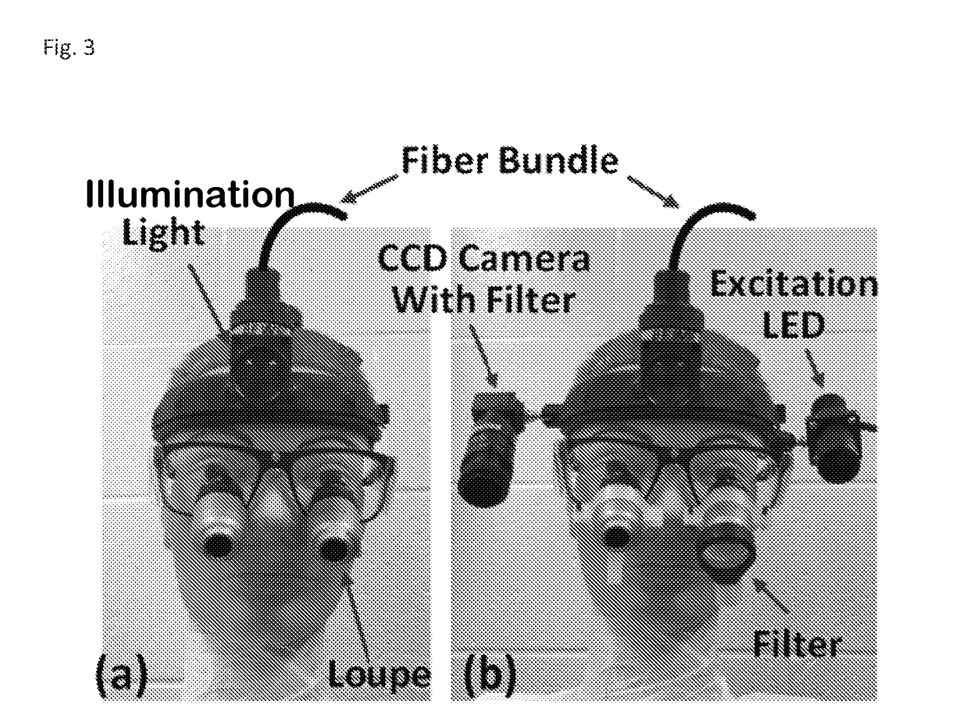
FIG. 3 shows (a) a commercial gical eye loupe (b) prototype of the fluorescence imaging device.

As depicted in FIGS. 1 and 2, the mounted device comprises a dual light source 20 aimed along the same direction as the housing, i.e. toward the same end as the wearer's eye and aimed in the same direction as the wearer's view. The dual light source emits a visible light 21, such as a white light, and an exciting light 22 that triggers the dye to fluoresce. Both light sources, 21 and 22, can be passed through a lens 23, before passing through a beam splitter 50 and focused on the target tissue 200. The lens 23 may optionally be adjustable such that the level of magnification and the focus can be altered by a user.

A camera 30 may also be introduced to the mounted portion. The camera 30 may be connected with the path of the dual light source 20 such that both share the same point of focus, i.e., both aim at overlapping areas (230, 240, 250) on the target tissue 200. The camera can share a combined field of view by being directed through a beam splitter 50 to share a significantly overlapping area of that of the dual light source, see. e.g. 230, 240, 250. The camera can be angled by the beam splitter to share the same view as that offered by the eyepiece. Collectively, the camera, the eyepiece and the light source offer a ROI (region of interest) 220 on the target tissue 200 with a diameter of between 5 to 10 cm.

The eyepiece housing body 120 is directed such that the wearer can visualize the target tissue 200. The body 120 may include a zoom lens 121 and a filter and/or a ND filter film 60 to allow the wearer to see the target tissue 200 clearly and enlarged. The filter and/or ND filter film 60 can be connected via a hinge 130, to allow the user to introduce or exit them from the users field of view 250. The zoom lens 121 may optionally be adjustable such that the level of magnification and the focus can be altered by a user.

The eyepiece housing body 120 and the camera 30 have a larger area field of view (FOV) 250 than that of the areas generated by the visible light 21, 230 and the excitation light 22, 240 from the dual light source 20. Operation of each light can be controlled by connection of each to a control unit 80. Optionally, a foot pedal 90 may be linked to the control unit 80 to allow the user to operate the each light source without having to look away from the target tissue 200. The visible light source 21 can be generated by either LEDS or byfiber-coupled light with filters. Those skilled in the art will appreciate that the light source need not be limited to two, such as in instances where a further fluorescent dye is introduced to differentiate further tissue. For example, two compact LEDs can be assembled with one single lens 23 for fluorescein excitation and white-light illumination. LED sources are be switchable using a foot pedal 90 and their intensities will be optimized by allowing for the variation of driving currents as controlled by an A/D board in the Control Unit 80 (FIG. 1). The modular design further allows for easy switching of source and detector modules for imaging other fluorescent dyes with emission light in the visible (400-700 nm) range, such as 5-aminolevulinic acid (5-ALA) and methylene blue, which can be used to detect various tumors in brain, breast, lung, eye, and oral cavity. Particularly, the use of 5-ALA has shown survival benefits for MG patients. Other dye and filter/wavelength combinations include blue fluorescent protein (BFP) at 390 nm, Tetramethylrhodamine Isothiocyanate (TRITC) at 542 nm, cyan fluorescent protein (CFP) at 434 nm, wild-type green fluorescent protein (WTGFP) at 445 nm, green fluorescent protein (GFP) at 469 nm, fluorescein isothiocyanate at 475 nm, yellow fluorescent protein (YFP) at 497 nm, Texas Red (TXRED) at 559 nm and cycanine (CY3.5) at 565 nm.

For real-time capture of fluorescence images, a light-weight camera 30, such as a CMOS camera, equipped with a zoom lens 31 and a removable long-pass filter 32 can be connected to the Control Unit 80. The LEDs and CMOS camera will share the same optical path using a dichroic beam splitter 50 (FIG. 2) and attached to the high magnification surgical eye loupes 120, such as through a fully lockable articulated ball and socket mount. One pair of long-pass filters 60 sitting in a custom-designed hand-flippable frame 130 will be also attached to the loupes, permitting an easy change (by flipping the frame up or down) of ocular visualization from fluorescence to white-light view. A thin neutral-density (ND) filter film with an appropriate transmission rate can be added in the loupe path to compensate for light loss in the camera path due to the beam splitter so that the surgeon's eyes and the camera will detect the same amount of fluorescent light for an identical visualization of tumor tissues. Many of the components can be manufactured to be lightweight, such as by using a 3D printer. As weight may be an issue other tiny cameras can be employed such as the Spy Camera (Adafruit, China) to further minimize the weight/size and increase the detection sensitivity. Although it may not be functionally necessary, a head support bracket 110 may be used to stabilize the loupes (FIG. 4a).

A user-friendly software graphical interface can setup parameters and control the hardware easily by the computer 70 (FIG. 1), such as switching alternatively between the two LEDs (in parallel with the foot pedal 90 control), controlling light intensities, adjusting camera parameters, and setting a fluorescent intensity threshold to identify tumor tissues argins. Furthermore, fluorescence images may be continuously recorded by the computer and displayed on the monitor.

Many factors may affect the performance/accuracy of our new device, such as the LED wavelength/intensity, the quality of lenses, filters, eye loupes, and camera, the alignment of the illumination and visualization, and the mechanical components/structure. The light intensity for fluorescein excitation, for example, must be carefully balanced by generating sufficient fluorescence while avoiding dye photobleaching and phototoxicity. The filter should be carefully selected as it performs a critical function in separating the fluorescence emission photons from the more-intense excitation light field. Furthermore, the eye loupes and CMOS camera should be aligned to the same focus and field-of-view (FOV), and their optical paths should be matched (by adding an optimal neutral density filter film, see FIG. 1) to achieve an identical visualization of the tumor tissues.

The present invention also provides methods of using the device described herein. The methods include administering a fluorescent dye to a subject and operating the device during surgery to assist in tissue resection.

For example, at the induction of anesthesia, subjects receive an appropriate dose of fluorescent dye, such as 5 mg/kg of intravenous sodium fluorescein. Surgery is performed with the operating room light dimmed for optimum reproduction of the fluorescent light. Tissue removal is continued until no fluorescent area is visualized. In cases located near or in the proximity of cortical or subcortical eloquent areas, neurophysiological monitoring can be performed.

To discriminate between clear tumor tissue and the peritumoral areas (gliosis or tumor cell infiltration), histopathological analysis of biopsied samples taken from the tumor margins can be performed according to standard procedures and classified on the basis of the current 2016 WHO classification. When appropriate, IDH1 immunostaining can also be conducted to highlight rare infiltrating tumor cells.

Compared to the standard operative microscope device (FIG. 3), the new loupe-based device for visualizing fluorescence (FIG. 1) provides surgeons an easier and more comfortable tool for real-time imaging of tumor margins during surgery. The wearable ergonomic device allows a greater range of movement, less obstruction, and faster operation, which in turn reduces surgery time.

Examples

Prototype

A high-intensity blue LED light source (peak wavelength: 470 nm, Thorlabs) was attached to a headlight support bracket (Halogen III Sport, BFW) for fluorescein excitation, and a long-pass filter (cut-off wavelength: 506 nm, Edmund Optics) was hooked in front of the loupes for fluorescence detection. This design allowed for easy switching between fluorescence (generated by the blue LED) and white-light (generated by the Xenon arc lamp coupled into a fiber bundle). In addition, a CCD camera (FL3-FW-20S4C-C, FLIR) equipped with another long-pass filter (>506 nm, Edmund Optics) was attached to the bracket (FIG. 2b) to record fluorescence images for data analysis (i.e., identifying tumor tissues).

Figure 4:
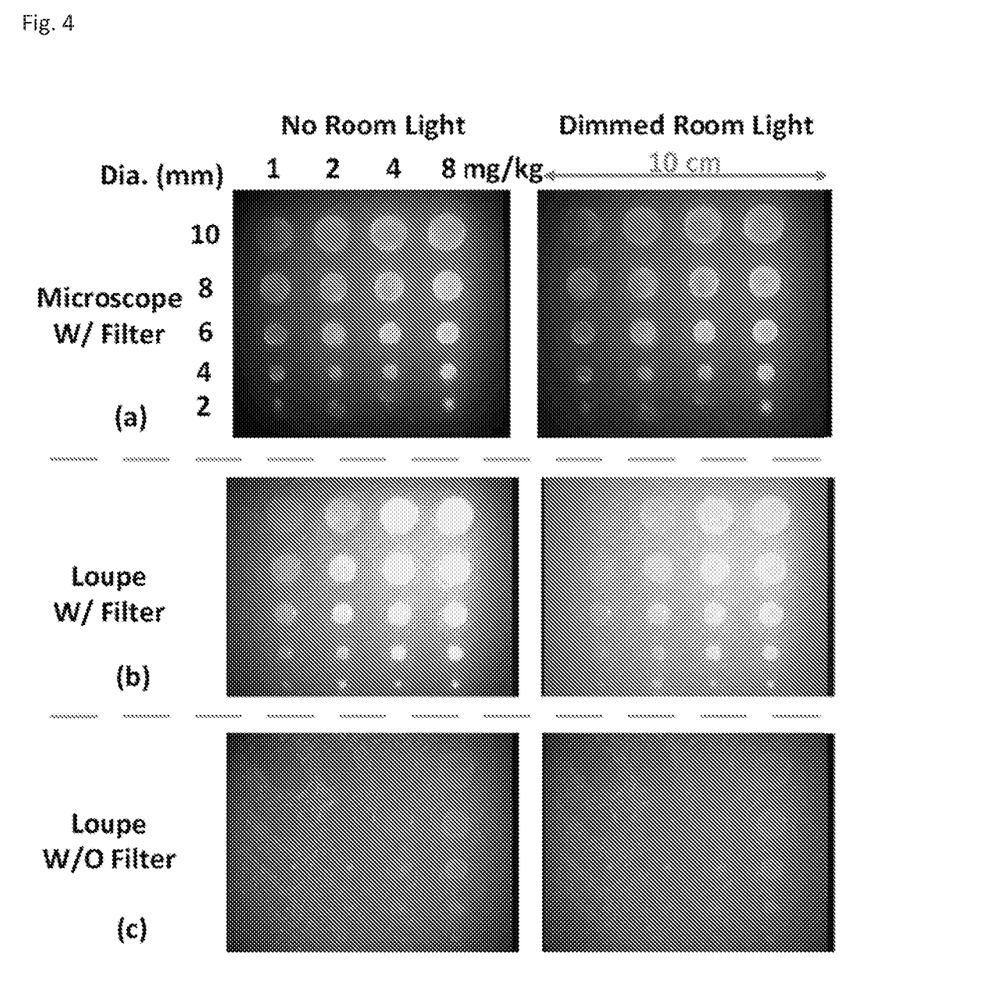
FIG. 4 shows Imaging results in tumor-simulating phantoms measured by Pentero 900 system with YELLOW 560™ (a) and our prototype device with a long-pass filter (b) and without (c).

The prototype was then tested in tumor-simulating phantoms with fluorescein contrasts under varied environmental conditions, and compared the results with the Pentero 900 with YELLOW560™ (FIG. 4). The bulk material used for making the phantom was acetal plastic, which effectively acts as a diffusive medium (like tissue). The phantom was fabricated using a 3D printer (Gigabot® 3.0) and consisted of holes and spaces to provide sufficient spread to test imaging sensitivity and spatial resolution. Experiments were performed by filling the holes with solutions of varying concentrations of fluorescein (1 to 8 mg/kg) to delineate real tumor tissues with different fluorescence contrasts. The smallest and largest holes were 2 and 10 mm in diameter respectively to mimic different sizes of tumors.

Fluorescence images of multiple phantom "tumors" were clearly observed by both devices, with or without dimmed room light (FIGS. 4a and 4b). The color difference between images of the operative microscope (FIG. 4a) and the loupe device (FIG. 4b) was primarily due to the differences in light sources (i.e., white light versus blue LED) and optical filters (i.e., >560 nm versus >506 nm) across the two systems. By contrast, when using our loupe device without the filter, fluorescent contrasts were hidden by the high-intensity excitation light (FIG. 4c). The holes with fluorescein concentrations as low as 1 mg/kg, and diameters as small as 2 mm were detected by both devices. These lower limits are generally sufficient to identify MG tissues, given that patients will receive 5 mg/kg of intravenous sodium fluorescein during surgery.

Human Visualization

Figure 5:
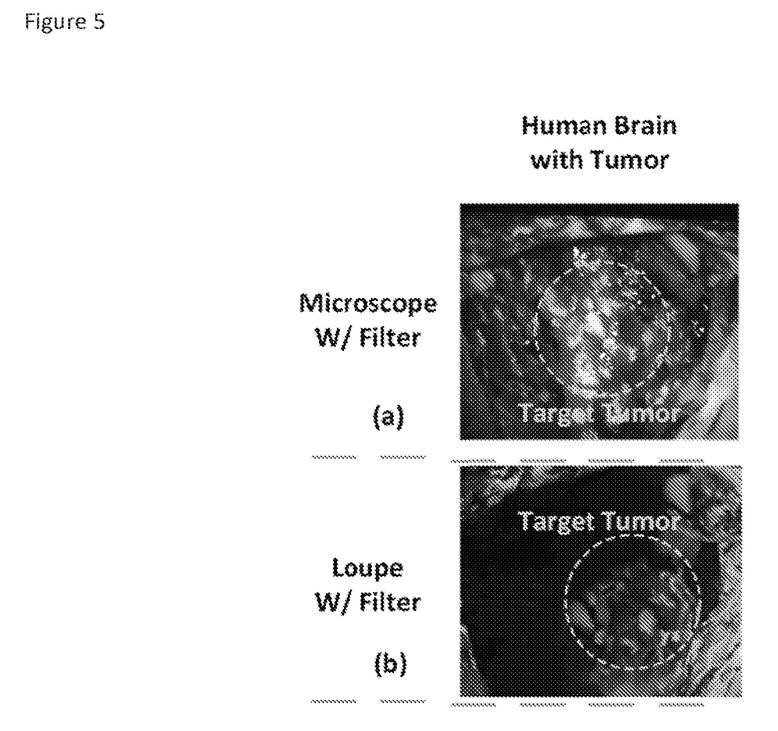
FIG. 5 shows a human brain with MG (right) measured by Pentero 900 system with YELLOW 560™ (a) and the prototype wearable device with an emission filter (b).

The device was tested in visualizing tissue for resection in a human patient. FIG. 5 shows fluorescence images taken from a patient's brain with MG. Note that the commercial Pentero 900 system utilizes a HILITE™ filtering technology to highlight the fluorescent signals on top of the color map (FIG. 5*a*). By contrast, our wearable device shows only a fluorescent map with a better fluorescence contrast on target tumors (FIG. 5*b*). Although such display difference leads to the color difference between the two images, similar fluorescent signals/dots are observed on the diffusive tumors.

While promising, the prototype device has not been optimized for easy and accurate use in the surgical setting. For example, the prototype device does not allow for changing from fluorescence view to color vision and vice versa. Also, the parts (e.g., light source, camera, filters) used are not optimal in terms of weight, size, quality, and ease-of-use. Most importantly, the new device needs to be further calibrated and evaluated against established standards for imaging quality and accuracy.

Assembly

For light sources, two compact LEDs (e.g., Blue: M470L3-470; White: MCWHL5, Thorlabs) are assembled with one single lens for fluorescein and white-light illumination to replace the fiber-coupled Xenon arc lamp. LED sources are switchable using a foot pedal and their intensities will be optimized by allowing for the variation of driving currents as controlled by an A/D board in the Control Unit (FIG. 1*a*).

For real-time capture of fluorescence images, a tiny lightweight CMOS camera (e.g., MU9PC-MBRD, Ximea) equipped with a zoom lens (e.g., 13VD5-50, PELCO) and a removable long-pass filter (e.g., 67-056, Edmund Optics) will be assembled and connected to the Control Unit. The LEDs and CMOS camera share the same optical path using a dichroic beam splitter (FIG. 2) and are attached to the high magnification surgical eye loupes (PrismPro, SurgiTel) using a fully lockable articulated ball and socket mount (e.g., TRB2, Thorlabs). One pair of long-pass filters (e.g., 67-072, Edmund Optics) sitting in a custom-designed hand-flippable frame will be also attached to the loupes, permitting an easy change (by flipping the frame up or down) of ocular visualization from fluorescence to white-light view. A thin neutral-density (ND) filter film with an appropriate transmission rate (Edmund Optics) can be added in the loupe path to compensate for light loss in the camera path due to the beam splitter so that the surgeon's eyes and the camera will detect the same amount of fluorescent light for an identical visualization of tumor tissues. Parts for these functional modules (i.e., LEDs, camera, and flippable filter frame) will be fabricated using lightweight plastic materials by a 3D printer, and are attached to the loupes for the stable, easy, and precise alignment of illumination and visualization.

A potential issue is the added weight of the functional modules on the eye loupes. Since most of the added weight is from the camera module, other small, lightweight, and highly-sensitive cameras such as the broad-level camera (MU9PC-MBRD, Ximea) and Spy Camera (Adafruit, China) may further minimize the weight/size and increase the detection sensitivity. Although it may not be functionally necessary, a head support bracket may be used to stabilize the loupes (FIG. 1).

Many factors may affect the performance/accuracy of this new device, such as the LED wavelength/intensity, the quality of lenses, filters, eye loupes, and camera, the alignment of the illumination and visualization, and the mechanical components/structure. The light intensity for fluorescein excitation, for example, must be carefully balanced by generating sufficient fluorescence while avoiding dye photobleaching and phototoxicity. The filter should be carefully selected as it performs a critical function in separating the fluorescence emission photons from the more-intense excitation light field. Furthermore, the eye loupes and CMOS camera should be aligned to the same focus and field-of-view (FOV), and their optical paths should be matched (by adding an optimal neutral density filter film, see FIG. 1) to achieve an identical visualization of the tumor tissues.

These key influencing factors can be evaluated, optimized, and calibrated (against the Pentero 900 with YELLOW 560™) using iterative tests in tumor-simulating phantoms with varying shapes/sizes of "holes" filled with different fluorescein concentrations (see the example shown in FIG. 2) to ensure appropriate performance and sufficient accuracy of our new device for identifying low levels and small sizes of fluorescence contrast targets ("diffusive tumors"). Further developments can be performed by filling up the holes in phantoms with diffusive solutions of Intralipid and fluorescein, which confer absorption and scattering values closer to brain tissue. These phantoms can be imaged using both the loupe-based device and the prototype system. Accordingly, these key influencing factors can be readjusted and optimized so that the loupe-based device achieves the same level of accuracy as the prototype system. Note that the commercial 900 system utilizes a HILITE™ filtering technology to highlight the fluorescent signal and outline the tumor contour/margin. Based on these comparison measurements, a fluorescence intensity threshold will be determined for our loupe-based device to differentiate "diffusive tumors" from healthy tissue (i.e., outlining tumor contours/margins).

After systematic optimization/calibration, the phantom tests can be repeated multiple times (e.g., 5 times) to characterize device performance, operator-dependent characteristics, imaging quality, and measurement accuracy/reproducibility.

A further potential issue is that using the beam splitter can significantly reduce the light intensity level (by ~50%) for fluorescein excitation. If necessary, more LEDs or a small laser diode (e.g., L488P60, 488 nm, Thorlabs) may increase the light power.

References

1. National-Brain-Tumor-Society. Tumor types: understanding brain tumors. http://braintumor.org/brain-tumor-information/understanding-brain-tumors/tumor-types/. 2016.
2. Kuhnt et al. *Neuro Oncol.* 2011; 13:1339-48.
3. Lacroix et al. *J Neurosurg.* 2001; 95:190-8.
4. McGirt et al. *J Neurosurg.* 2009; 110:156-62.
5. Stummer et al. *J Neurooncol.* 2012; 108:89-97.
6. Stummer et al. *Lancet Oncol.* 2006; 7:392-401.
7. Aldave et al. *Neurosurgery.* 2013; 72:915-20; discussion 920-1.
8. Picart et al. *Neurochirurgie.* 2017; 63:189-196.
9. Rosenthal et al. *Ann Surg.* 2015; 261:46-55.
10. Acerbi et al. *Neurosurg Rev.* 2014; 37:547-57.
11. Belykh et al. *Front Surg.* 2016; 3:55.
12. Acerbi et al. *Acta Neurochir (Wien).* 2013; 155:1277-86.
13. Decker et al. Intraoperative use of fluorescein for malignant glioma resection differentiates tumor from normal brain tissue based on histopathologic analysis. Paper presented at: 19th Annual Scientific Meeting of the Society for Neuro-Oncology; 2014 Miami, Fla.

14. Zong et al. *Expert Rev Mol Diagn.* 2012; 12:383-94.
15. National-Brain-Tumor-Society. Quick brain tumor facts. http://www.abta.org/about-us/news/brain-tumor-statistics/. 2017.
16. Mariatto et al. *J Natl Cancer Inst.* 2011; 103:117-28.
17. Shang et al. *Journal of biomedical optics.* 2013; 18:105002
18. Hartov et al. *Neurosurgery.* 2008; 62:91-9; discussion 99-101.
19. Albert et al. *Neurosurgery.* 1994; 34:45-60; discussion 60-1.
20. Moore et al. *Journal of Neurosurgery.* 1948; 5:392-398.
21. Mela et al. *Methods Mol Biol.* 2016; 1444:85-95.
22. Mondal et al. *Scientific reports.* 2015; 5:12117.
23. Liu et al. *Transl Res.* 2013; 162:324-31.
24. Brain-Tumour-Charity. 5-ALA gets FDA approval. https://www.thebraintumourcharity.org/media-centre/news/research-news/5-ala-gets-fda-approval/. 2017.
25. Frederic et al. Proceedings of SPIE—The International Society for Optical Engineering. 2009; DOI: 10.1117/12.808928
26. Ghauharali et al. *J Microsc.* 2000; 198 (Pt 2):88-100.
27. Michalet et al. *Philos Trans R Soc Lond B Biol Sci.* 2013; 368:20120035.
28. Jacques et al. *Physics in medicine and biology.* 2013; 58:R37-61.
29. Huang et al. *Journal of biomedical optics.* 2015; 20:075008.
30. Huang et al. *Applied optics.* 2015; 54:880846.
31. Huang et al. *Medical physics.* 2015; 42:4000-6.
32. He et al. *Journal of biomedical optics.* 2015; 20:86003.
33. Lin et al. *Applied physics letters.* 2014; 104:121103.
34. Li et al. *Scientific reports.* 2013; 3:1358.
35. Done et al. *Journal of biomedical optics.* 2016; 21:085004
36. Huang et al. *J Biomed Opt Lett.* 2016; 21:080501.
37. Huang et al. *IEEE Transactions On Medical Imaging DOI:* 101109/TMI20172708661. 2017; 36:2068-2076.
38. Agochukwu et al. *Plast Reconstr Surg.* 2017; 140:26-31.
39. Cordella et al. *Neurol Sci.* 2013; 34:63-70.
40. Hoshide et al. *World Neurosurg.* 2016; 94:561-562.
41. Louis et al. *Acta Neuropathol.* 2016; 131:803-20.
42. Gilbert et al. *Acta Neuropathol.* 2014; 127:221-33
43. Neltner et al. *J Neuropathol Exp Neurol.* 2012; 71:1075-85.
44. Attems et al. *Alzheimers Res Ther.* 2014; 6:85.
45. Pepe. *The statistical evaluation of medical tests for classification and prediction.* New York: Oxford; 2003.
46. Efron B and R. T. *An introduction to the bootstrap.* New York: Chapman & Hall; 1993.
47. Yang et al. *IEEE transactions on medical imaging.* 2011; 30:1921-32.
48. Mannas et al. *J Clin Neurosci.* 2014; 21:121-3.
49. Dan et al. *Pharm Res.* 2015; 32:1615-25.
50. Villano et al. *Neuro Oncol.* 2014; 16:1155-6.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled. Further, all references cited herein are incorporated by reference in their entirety.

The invention claimed is:

1. A loupe-based surgical device for fluorescent and visible light visualization of a tissue resection, comprising:
    at least one eye loupe housing body, adapted for wearing on a head of a user, with a lens carried thereon to allow a user to view a target tissue area of the tissue resection;
    a dual light source also adapted to wear on the head of the user, the dual light source, including (a) a visible light source adapted for illuminating the target tissue area with visible light and (b) an excitation light source adapted for exciting a fluorescent dye in the target tissue area and causing the fluorescent dye to emit a fluorescent light in the visible light range viewable through the lens by the user; and
    an optical filter, held in a flippable frame carried on the at least one eye loupe housing body, wherein the optical filter allows the user to easily change ocular visualization between fluorescence and white light view.

2. The loupe-based surgical device of claim 1, further including a camera carried on the at least one eye loupe housing body.

3. The loupe-based surgical device of claim 2, wherein the camera is connected to a computer.

4. The loupe-based surgical device of claim 2, further including a beam splitter.

5. The loupe-based surgical device of claim 4, wherein the optical filter is positioned between the camera and the beam splitter.

6. The loupe-based surgical device of claim 5, wherein the dual light source includes at least one light emitting diode.

7. The loupe-based surgical device of claim 5, wherein the dual light source includes a xenon light source.

8. The loupe-based surgical device of claim 5, wherein the dual light source includes a light emitting diode and a xenon light source.

9. The loupe-based surgical device of claim 1, further including a head support bracket attached to the at least one eye loupe housing body to stabilize the at least one eye loupe housing body on the head of the user.

10. The loupe-based surgical device of claim 1, wherein a wavelength of the excitation light is selected to excite a fluorescent dye selected from a group of visible dyes consisting of 5-aminolevulinic acid (5-ALA), sodium fluorescein, methylene blue, blue fluorescent protein (BFP), Tetramethylrhodamine Isothiocyanate (TRITC), cyan fluorescent protein (CFP), wild-type green fluorescent protein (WTGFP), green fluorescent protein (GFP), yellow fluorescent protein (YFP), Texas Red (TXRED) and cycanine (CY3.5).

11. The loupe-based surgical device of claim 1, wherein the dual light source includes at least one light emitting diode.

12. The loupe-based surgical device of claim 1, wherein the dual light source includes a light emitting diode and a xenon light source.

13. The loupe-based surgical device of claim 1, wherein the dual light source is connected to a control unit that is optionally connected to a foot pedal.

14. The loupe-based surgical device of claim 1, wherein the lens is (a) a magnifying lens, (b) a zoom lens or (c) a magnifying lens and a zoom lens.

15. The loupe-based surgical device of claim 1, wherein said filter comprises ND filter.

16. A method for visualizing tissue resection, comprising:
    administering a fluorescent dye to a subject receiving tissue resection;

placing the loupe-based surgical device of claim 1 on a head of a surgical user operating on the subject; and operating the dual light source to (a) illuminate the target tissue area with visible light and (b) excite the fluorescent dye in the target tissue area so as to cause the fluorescent dye to emit a fluorescent light in the visible light range viewable through the lens by the user.

17. A method of visualizing a tissue resection, comprising;

administering a fluorescent dye to a subject receiving tissue resection;

directing a dual light source, carried on at least one eye loupe housing body adapted for wearing on a head of a user, toward a target tissue area;

using visible light from the dual light source to illuminate the target tissue area of the tissue resection;

using excitation light from the dual light source to excite the fluorescence dye and produce visible fluorescent light at the target area of the tissue resection;

viewing the visible fluorescent light and the target tissue area through a lens carried on the at least one eye loupe housing body; and using an optical filter, held in a flippable frame carried on the at least one eye loupe housing body, to easily change ocular visualization between fluorescence and white light view.

18. The method of claim 17, including visually identifying a tumor in the target tissue area by means of the visible fluorescent light emitted by the fluorescent dye in response to the excitation light.

\* \* \* \* \*